United States Patent [19]

Zeibig et al.

[11] 4,170,794
[45] Oct. 16, 1979

[54] BONE JOINT ENDOPROSTHESIS

[75] Inventors: Anton Zeibig, Ottensoos, Fed. Rep. of Germany; John T. Scales, Stanmore, England

[73] Assignee: Rosenthal Technik AG, Bavaria, Fed. Rep. of Germany

[21] Appl. No.: 901,083

[22] Filed: Apr. 28, 1978

[51] Int. Cl.² ............................................. A61F 1/24
[52] U.S. Cl. ...................................... 3/1.91; 3/1.913; 128/92 C; 128/92 CA
[58] Field of Search ................................. 3/1.9–1.913; 128/92 C, 92 CA

[56] References Cited

U.S. PATENT DOCUMENTS

| 3,102,536 | 9/1963 | Rose et al. | 3/1.913 X |
| 3,973,278 | 8/1976 | Shersher | 3/1.912 |
| 4,012,795 | 3/1977 | Doore et al. | 3/1.91 |

FOREIGN PATENT DOCUMENTS

| 2059381 | 3/1972 | Fed. Rep. of Germany | 3/1.913 |
| 2340734 | 2/1975 | Fed. Rep. of Germany | 3/1.912 |
| 2451275 | 5/1976 | Fed. Rep. of Germany | 3/1.913 |
| 1334584 | 10/1973 | United Kingdom | 3/1.912 |
| 1371335 | 10/1974 | United Kingdom | 3/1.913 |

*Primary Examiner*—Ronald L. Frinks
*Attorney, Agent, or Firm*—Ostrolenk, Faber, Gerb & Soffen

[57] ABSTRACT

A bone joint endoprosthesis comprises a spherical body of the joint with hole in it for receiving a shaft spigot; a shaft is embedded in bone; the shaft has a spigot which is received in the hole; a spreader, comprised of a material that swells when it is wetted, is wrapped over the spigot in the hole or is inside the spigot and the spreader expands radially in the hole or inside the spigot to secure the joint; shaping and profiling of the spigot and the wall of the hole for effective retention of the spreader are disclosed.

18 Claims, 4 Drawing Figures

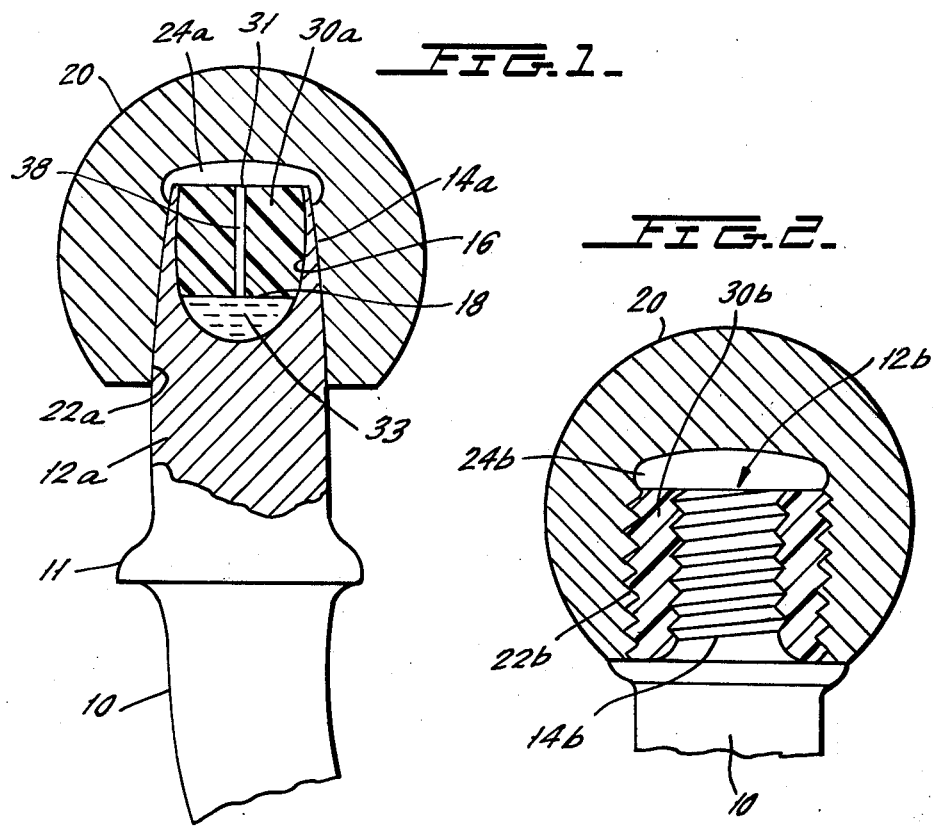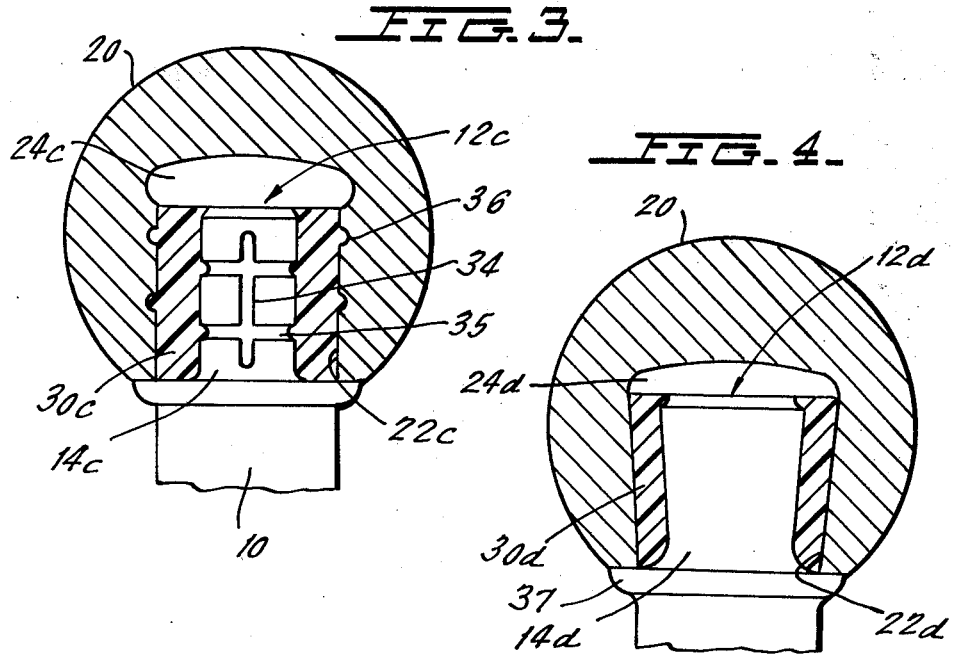

BONE JOINT ENDOPROSTHESIS

BACKGROUND OF THE INVENTION

The invention relates to a bone joint endoprosthesis, particularly useful as a hip joint prosthesis, in which the body of the joint is held on a shaft by a clamping means.

Federal Republic of Germany published specification DT-OS No. 24 51 275 describes a joint endoprosthesis of this type in which a spigot comprised of a metal alloy is made an integral part of a shaft, and the shaft can be inserted into the femur. The spigot is conically shaped, with a taper ratio between 1:10 and 1:20. The spigot is fitted in a self locking manner into a matching conical bore hole that is formed in a spherically shaped body of a joint. The body of the joint is comprised of sintered ceramic material. This arrangement provides a rigid bond between the body of the joint and the spigot. Furthermore, it avoids the risk of cracking of the body of the joint under too high a load. It has, however, been found that these benefits can best be achieved under particularly favorable conditions and only if both the conical spigot and the matching hole in the body of the joint have been finished to a very high accuracy.

Federal Republic of Germany published specification DT-OS No. 23 18 459 describes a joint endoprosthesis, in which a spherical body of a joint has an internal self-tapping screw thread for fitting on a cylindrical spigot which has been produced as part of the head of a femur. In this way, the screw threaded body of the joint is secured by formlocking so that it cannot be pulled off the spigot in an axial direction. But, unintentional unscrewing of the body of the joint from the spigot is prevented only by clamping forces, and their effect is not sufficiently reliable. The body of the joint could be further secured on the spigot by means of a radially extending screw. But, the drilled hole required for this purpose would unduly weaken the body of the joint and the spigot.

Similar considerations apply to the joint endoprosthesis described in German published specification DT-OS No. 23 40 734, in which a shaft, which can be inserted into the femur, has an externally threaded spigot and where a spherical body of a joint of an oxide ceramic is screwed onto the spigot.

SUMMARY OF THE INVENTION

The object of the invention is to provide a joint endoprosthesis of the type mentioned above wherein the bond between the body of the joint and the spigot is sufficiently strong and wherein the risk of cracking of the body of the joint under too high a load is avoided.

The invention comprises producing the clamping forces by placing a spreader having a sleeve shape, or having the like shape, and which swells in the presence of liquid, in the body of the joint, in addition to the spigot. The spreader is shaped and placed such that swelling of the spreader clamps the spigot inside the hole in the body of the joint.

A sufficient supply of parenchymatous fluid is supplied to the spreader so that following implantation of the prosthesis, the spreader swells by the desired amount and thereafter remains in the swollen condition. The magnitude and direction of the spreading or clamping forces produced during swelling can be fixed in the desired way by appropriate shaping, profiling and dimensioning of the spreader and the spigot and the hole in the body of the joint.

The invention can be used with various shape spigots, including cylindrical spigots having circular or non-circular, for example elliptical bases, prismatic shape spigots, spigots in the form of truncated cones having circular or non-circular bases and spigots in the form of truncated pyramids. The spigot may be an extension of a shaft which can be inserted into a bone or the spigot itself may be shaped as a body of a joint. In the sense of the invention, a part of a prosthesis which, for example, as shown in German published specification DT-OS No. 23 18 459, is externally partially shaped as a spigot. This spigot is embedded in the hip bone and the spigot has an internally spherical surface forming the joint socket.

Independent of the details of shape and function of the spigot, the spreader may be in the shape of a sleeve, which wraps around the spigot. When this spreader is in its swollen condition, it is exerting radial forces on the spigot, on the inside of the sleeve, and on the surrounding body of the joint outside of the sleeve. In this case, direct contact between the spigot and the body of the joint is not required. This can be important for avoiding electrolytic corrosion where the spigot and the body of the joint are both made of metal.

The sleeve-shaped form of the spreader can be further developed so that when the spreader swells, it is anchored by form-locking due to unevenness formed on the surface of the spigot and/or on the inner wall of the hole in the body of the joint. The unevenness may for example be in the form of a series of circular or paraxial grooves in the opposing walls of the spigot and the body of the joint. Such grooves are shown in German published specification DT-OS No. 21 34 318 where they serve to accept cement or glue.

If the spigot is externally threaded and the hole in the body of the joint is internally threaded, in a further embodiment, the sleeve-shaped spreader, before it swells, already has an internal thread which is screwed onto the spigot and has an external thread which is screwed into the body of the joint. In this way the spreader forms a bond, which is form-locking in the axial direction, between the spigot and the body of the joint before the spreader is swollen. Additionally, the radial clamping or spreading forces produced by swelling of the spreader reliably prevent relative rotational movement between the already axially form locked spigot and body of the joint. Of course, it is possible by means of additional unevenness of the type described above, for example paraxial grooves in the spigot and/or in the body of the joint, to additionally assure that swelling of the spreader and the above noted form-locking securely prevent rotation.

Alternatively, the inner and outer surfaces of the sleeve-shaped spreader may expand toward the end of the spigot and make contact with complementary surfaces of the spigot and the body of the joint. This restrains longitudinal expansion of the spreader and correspondingly enhances its radial expansion which is the expansion that exerts a clamping force. This embodiment presupposes that the spreader can be deformed to the required degree during fitting and prior to its swelling.

According to Federal Republic of Germany Patent Application No. P 24 46 478.8, the spigot has a recess extending to its end for receiving the spreader and the spreader is placed inside the recess in the spigot, rather than around the spigot. The spreader produces radial forces during swelling that press only in an outward direction against the surrounding spigot so that the spigot, which is of circular cross-section, is expanded and pressed against the body of the joint.

Escaping of the spreader in an axial direction can be prevented in several ways. For example, the end of the spigot may be flanged inwardly. The spigot recess may also have an unevenness on its inner surface, for example circular grooves, and the spreader becomes anchored in these grooves by form-locking during swelling, as described above in connection with the sleeve-shaped spreader. It is particularly useful if the spreader tapers wider in shape toward the deep end of the recess, and if the recess in the spigot is of complementary shape.

It is additionally advantageous if the spreader, which is arranged in the recess in the spigot, has at least one channel connecting a reservoir of liquid at the bottom of the recess in the spigot to the end of the spreader which is furthest away from the bottom of the recess.

In all of the foregoing embodiments, the spreader may have a noncircular cross-section to match the cross-section of the spigot and/or the body of the joint.

The spreader may, at least partially, be comprised of polyamide. Other organic plastics which can swell sufficiently are also suitable for making the spreader. However, the spreader can also, at least partially, be comprised of inorganic material with swelling properties. For example, there are known inorganic materials which swell by crystalline attachment of water.

Independent of whether essentially organic or inorganic material is used for the spreader, the spreader may contain fibers embedded in it and extending in the longitudinal direction of the spigot to reduce swelling of the spreader in this direction. This causes the spreader to swell essentially in the radial direction only.

BRIEF DESCRIPTION OF THE DRAWINGS

Preferred embodiments of the invention are now described with reference to the accompanying drawings in which:

FIG. 1 shows a hip joint endoprosthesis in axial cross-section according to a first embodiment of the invention;

FIG. 2 shows the same view of a second embodiment of the invention;

FIG. 3 shows the same view of a third embodiment of the invention; and

FIG. 4 shows the same view of a fourth embodiment of the invention.

DESCRIPTION OF THE PREFERRED EMBODIMENTS

Each of the hip joint prostheses shown in FIGS. 1 to 4 has a shaft 10 comprised of a metal alloy. Shaft 10 can be driven into a femur to the depth of a collar 11 on the shaft. Above collar 11, the shaft 10 terminates in an integral spigot 12.

In the embodiment shown in FIG. 1, the upper part of spigot 12a has an outer surface 14a, which is in the shape of a truncated cone. There is a recess 16 extending in form the upper end of the spigot. The wall defining the upper part of the recess 16 also is in the shape of a truncated cone, and that wall tapers in the same direction as, but with a cone angle somewhat smaller than, the outer surface 14a of the spigot. The recess 16 has a rounded bottom 18 with a comparatively large radius of curvature.

A spherical body of a joint 20 of high purity aluminum oxide is fixed on a spigot 12a with a press fit. For receiving the spigot 12, the body of the joint 20 has a radially extending hole 22a, the side wall of which is tapered at the same angle as the outer surface of the spigot. At its inner end, the hole 22a is enlarged at 24a.

Recess 16 is largely filled with a spreader 30a which is a solid body or plug comprised of a material which can swell in the presence of liquid. The material of the spreader of this embodiment and of all of the other embodiments has this same characteristic. All of the spreaders 30 may be comprised of a polyamide, for example. Other suitable organic materials may be used. Alternatively, a suitable inorganic material with the desired properties may be used.

The spreader 30 in this embodiment and in all of the other embodiments may have longitudinally extending, inflexible fibers 38 of any suitable material embedded in it for minimizing longitudinal expansion of the spreader when it swells. In the prosthesis of the invention, the more useful expansion is radial, whereby when the longitudinal expansion is restrained, the radial expansion is enhanced.

Spreader 30a in FIG. 1 has an axial channel 31 extending therethrough which is of comparatively small diameter. Channel 31 transmits liquid from a reservoir 33 at the bottom 18 of recess 16 to all regions of the spreader 30a. This causes the spreader 30a to swell uniformly over the whole length. Over its whole length, the spreader applies an essentially uniform pressure on the inner wall of spigot 12a. This firmly presses the truncated cone shape outer surface 14a of the spigot 12a against the wall of the hole 22a and this ensures a strong friction-locking fit between the spigot 12a, and the body 20 of the joint. There might not be a reservoir, like reservoir 33, in the other embodiments. Therefore, the liquid that is supplied to the other spreaders 30 for causing them to swell must be supplied by injection through a hole in the body, by capillary action or by another appropriate liquid application technique.

In the hip joint prosthesis shown in FIG. 2, the upper part of the spigot 12b has an external thread 14b. A sleeve-shaped spreader 30b, which is also comprised of a material which swells in the presence of liquid, is screwed into the spigot 12b. The spherical body of a joint 20 has an internally threaded hole 22b in which the body of the spreader 30b is screwed. The upper end of the hole 22b comprises an enlarged opening 24b. The spreader 30b is initially formed with an internal and an external thread, which enables it to be screwed onto the spigot 12b. When the spreader swells, it more securely engages both the spigot 12b and the body 20, thereby preventing subsequent unscrewing. Furthermore, the threaded interengagement inhibits longitudinal shifting of the spreader, whereby when it swells, the expansion is mostly radial.

In the hip joint prosthesis shown in FIG. 3, the upper part of the spigot 12c has an essentially cylindrically shaped outer surface 14c in which are defined interacting longitudinally extending grooves 34 and circumferentially extending grooves 35. The spigot 12c is surrounded by a sleeve-shaped spreader 30c which is comprised of a material which can swell in the presence of liquid. A spherical body of a joint 20 is slipped over the spreader 30c. The body of the joint 20 has an essentially cylindrically shaped, radially inwardly extending hole 22c which receives the spreader 30c. The side wall of this hole also has both longitudinally extending and transverse or even fully circumferential grooves 36 formed in it. The upper end of the hole 22c comprises an enlarged opening 24c. The body of the spreader 30c penetrates into the grooves 34, 35 and 36 by swelling. The grooves of the spigot and of the body of the joint engage the spreader 30c and inhibit its expansion longitudinally, whereby the principal swelling is desirably in the radial direction.

In the hip joint prosthesis shown in FIG. 4 the spigot 12d has a generally frustoconical outer surface 14d, which has its larger diameter at the upper end of the spigot, contrary to the first embodiment of FIG. 1. The outer surface 14d is surrounded by a sleeve-shaped swellable spreader 30d, which is shaped to generally conform to the external shape of the spigot 12d and the wall of the hole 22d. Accordingly, both the inner and the outer surfaces of the spreader are tapered, in the shape of a truncated cone. The body of the joint 20 has a radially extending hole 22d defined in it, which expands inwardly in the shape of a truncated cone. The upper end of the hole 22d comprises an enlarged opening 24d. The body of the joint 20 is slipped over the spreader 30d. The material of the spreader is sufficiently flexible and the diameter of the widest end of the spigot 12d is narrower than the outer end of the hole 22d so that the spigot and the spreader may be inserted into the hole 22d. When the spreader 30d expands to its normal size, which occurs upon its swelling, the spreader 30 completely fills the annular space between the outer surface 14d of spigot 12 and the wall of hole 22d in the body of the joint.

In the fourth embodiment especially, but also in the second and third embodiments to a lesser extent, the spreader 30d, and particularly its internal and external surfaces expand axially of the spigot as the spreader swells and eventually make secure sealing contact with the collar 37 on the spigot 12d, which collar is located just beneath the joint of a body 20 when the joint is emplaced over the spreader. This, along with longitudinally extending fibers 38 embedded in the spreader 30, if such fibers are used, restrains longitudinal expansion of the spreader, thereby enhancing its desired radial expansion.

Although the present invention has been described in connection with preferred embodiments thereof, many variations and modifications will now become apparent to those skilled in the art. It is preferred, therefore, that the present invention be limited not by the specific disclosure herein, but only by the appended claims.

What is claimed is:

1. A bone joint endoprosthesis, comprising:
   a body of the bone joint; said body having a side and having a hole extending into said body from said side thereof; said body hole being defined in said body by a side wall;
   a shaft for being received in a bone; said shaft having an end with a spigot defined thereon; said spigot being received in said body hole and being shaped to fit therein;
   a spreader in said body hole; said spreader being comprised of a material that swells in the presence of a fluid; said spreader being placed such that as it swells, it applies clamping forces to hold said body of the joint securely to said spigot.

2. The bone joint endoprosthesis of claim 1, wherein said spreader comprises a sleeve around said spigot and in said hole.

3. The bone joint endoprosthesis of claim 2, wherein said spigot has an exterior and said spreader is in engagement with said exterior of said spigot; said spigot being inside said spreader; said spreader being in engagement with said side wall of said hole; whereby said spreader exerts radial forces against said spigot and said side wall of said hole in said joint body upon swelling.

4. The bone joint endoprosthesis of claim 3, wherein at least one of the exterior of said spigot and said side wall of said hole has an unevenness so that as said spreader swells, it becomes anchored by form locking of said spreader in said unevenness.

5. The bone joint endoprosthesis of claim 4, wherein said unevenness comprises a screw thread.

6. The bone joint endoprosthesis of claim 4, wherein both of said spigot exterior and said hole side wall have an unevenness thereon.

7. The bone joint endoprosthesis of claim 6, wherein said unevenness comprises said spigot having an external thread defined on it and said side wall of said hole having an internal thread on it and said spreader being held to said threads when said spreader swells.

8. The bone joint endoprosthesis of claim 7, wherein prior to being swelled, said spreader has an internal thread and said spreader internal thread is screwed onto said spigot external thread and said spreader has an external thread and said spreader external thread is screwed into said joint body internally threaded side wall hole.

9. The bone joint endoprosthesis of claim 3, wherein said spigot includes a surface positioned to block longitudinal expansion of said spreader as said spreader swells.

10. The bone joint endoprosthesis of any one of claims 1 or 2, wherein said spigot has a respective particular cross-sectional shape and said hole in said joint body has a particular cross-sectional shape and said spreader prior to swelling, has a cross-sectional shape to mate with said spigot cross-sectional shape and with said joint body hole cross-sectional shape.

11. The bone joint endoprosthesis of claim 1, wherein said spigot has a recess in it in which said spreader is received, such that when said spreader swells, said spreader presses said spigot against said body hole side wall.

12. The bone joint endoprosthesis of claim 11, wherein said spigot has an end inside said body hole; said body of said spigot extends around said spigot recess.

13. The bone joint endoprosthesis of claim 12, wherein said spreader tapers narrower toward said spigot end, and said spigot recess tapers narrower in a complementary manner toward said spigot end.

14. The bone joint endoprosthesis of claim 12, wherein said spigot recess has a reservoir space at the bottom end thereof for containing fluid; said spreader having a channel therethrough which communicates with said reservoir space for transmitting fluid from said reservoir space through said spreader.

15. The bone joint endoprosthesis of any one of claims 1, 3 or 11, wherein said spreader is at least partially comprised of a polyamide.

16. The bone joint endoprosthesis of any one of claims 1, 3 or 11, wherein said spreader is at least partially comprised of an organic material.

17. The bone joint endoprosthesis of any one of claims 1, 3 or 11, wherein said spreader is at least partially comprised of an inorganic material.

18. The bone joint endoprosthesis of one of claims 1, 4 or 9, wherein said spreader contains fibers imbedded therein and extending in the longitudinal direction of said spreader and of said spigot, for reducing swelling of said spreader in the longitudinal direction thereof.

* * * * *